United States Patent
East et al.

(10) Patent No.: US 7,619,056 B2
(45) Date of Patent: Nov. 17, 2009

(54) THERMOSET EPOXY POLYMERS FROM RENEWABLE RESOURCES

(75) Inventors: Anthony East, Madison, NJ (US); Michael Jaffe, Maplewood, NJ (US); Yi Zhang, Harrison, NJ (US); Luiz H Catalani, Carapicuiba (BR)

(73) Assignee: New Jersey Institute of Technology, Newark, NJ (US)

( * ) Notice: Subject to any disclaimer, the term of this patent is extended or adjusted under 35 U.S.C. 154(b) by 201 days.

(21) Appl. No.: 11/809,034

(22) Filed: May 31, 2007

(65) Prior Publication Data

US 2008/0009599 A1    Jan. 10, 2008

Related U.S. Application Data

(60) Provisional application No. 60/810,512, filed on Jun. 2, 2006.

(51) Int. Cl.
*C08G 59/50* (2006.01)
*C07D 493/02* (2006.01)

(52) U.S. Cl. ...................... 528/421; 549/464
(58) Field of Classification Search .......... None
See application file for complete search history.

(56) References Cited

U.S. PATENT DOCUMENTS

| 3,041,300 | A | 6/1962 | Morrison |
|---|---|---|---|
| 3,272,845 | A | 9/1966 | Zech |
| 4,169,152 | A | 9/1979 | LeMaistre |
| 5,162,547 | A | 11/1992 | Roth et al. |
| 5,245,048 | A | 9/1993 | Rolfe et al. |
| 2003/0055142 | A1 | 3/2003 | Steckel |
| 2003/0163851 | A1 | 8/2003 | Kasukabe et al. |
| 2003/0212244 | A1 | 11/2003 | Hayes et al. |
| 2005/0137310 | A1 | 6/2005 | Gupta et al. |
| 2006/0069234 | A1 | 3/2006 | Kauffman et al. |
| 2006/0102871 | A1 | 5/2006 | Wang et al. |
| 2008/0021209 | A1* | 1/2008 | East et al. .................. 536/124 |

OTHER PUBLICATIONS

HCAPLUS accession No. 2004:188375 for Chinese Patent No. 1,370,789, Peng et al., Sep. 25, 2002, two pages*
Derwent accession No. 2003-076479 for Chinese Patent No. 1,370,789, Peng et al., Sep. 25, 2002, one page*

* cited by examiner

*Primary Examiner*—Robert Sellers
(74) *Attorney, Agent, or Firm*—Kent A. Herink; Emily E. Harris

(57) ABSTRACT

Novel thermoset epoxy polymers using the bisglycidyl ethers of anhydrosugars, such as isosorbide, isomannide, and isoidide, are disclosed. The bisglycidyl ethers are useful as substitutes for bisphenol A in the manufacture of thermoset epoxy ethers. The anhydrosugars are derived from renewable sources and the bisglycidyl ethers are not xenoestrogenic and the thermoset curing agents are likewise derived form renewable resources.

2 Claims, No Drawings

THERMOSET EPOXY POLYMERS FROM RENEWABLE RESOURCES

This application claims priority to U.S. Patent Application Ser. No. 60/810,512, filed Jun. 2, 2006.

STATEMENT OF GOVERNMENTAL INTEREST

This invention was made, at least in part, with United States governmental support awarded by the U.S. Department of Energy Grant No. DE-FC36-03GO13000. The United States Government has certain rights in this application.

BACKGROUND OF THE INVENTION

The invention relates to thermoset epoxy polymers and, more specifically, to thermoset polymers derived from renewable resources.

Thermoset epoxy polymers are widely used in numerous industries, like coatings, adhesives, composites and electronic components encapsulation, because of their largely infusible and insoluble properties following curing. An example of particularly widespread use is as a coating of food cans to protect the food from contact with the reactive metal of the can. A cured epoxy system typically consists of a base epoxy resin and one or more additional components like hardener, catalyst, reactive flexible molecules, reactive diluents and a variety of inert additives. Many of these components are derived from petroleum and as such are not renewable. A very common moiety in these systems is bisphenol A, which is a widely used building block molecule in several plastic materials and epoxy resins. Bisphenol A has been known to have esterogenic properties since the 1930's. Unfortunately, the chemical bonds that link bisphenol A in polymer structures are not completely stable and the polymer may slowly decay with time, releasing small amounts of bisphenol A into materials with which it comes into contact, for example food or water. Recent studies have shown the widespread presence of tiny amounts of bisphenol A in many parts of the environment. Even at minute levels it may still exert estrogen-like effects on living organisms.

Alternative molecules that are derived from renewable sources and do not have estrogen-like properties would have obvious utility, particularly in such markets as food can coatings. They would also reduce demands for petroleum. Possible replacements for bisphenol-A and other epoxy linkers are the bisanhydrohexitols, stable cyclic ether diols derived by dehydration of sugar alcohols. These sugar alcohols are in turn simply produced by reducing hexose sugars derived from several bio-renewable resources such as corn syrup. An additional advantage that may apply to such materials is their biodegradation to harmless products. Notable anhydrosugars useful in this context include isosorbide, isomannide, and isoidide, although other derivatives not necessarily derived from hexose sugars may also be of value and fall within the scope of this invention.

It is known to make intermediates for epoxy resins from bisanhydrohexitols such as their glycidyl ethers. Examples of this art are to be found in U.S. Pat. No. 3,272,845 (Zech, et al.) and U.S. Pat. No. 3,041,300 (Morrison) which both describe methods of making the bisglycidyl ethers of isosorbide, isomannide, and isoidide, collectively referred to in the patents as isohexides.

Such epoxy intermediates are frequently water-soluble. In accordance with the present invention, we have shown that with suitable epoxy resin hardeners it is possible to make cold-cure epoxies in aqueous solution which gel and set hard and may be subsequently baked to give a final cure resin.

SUMMARY OF THE INVENTION

The invention consists of epoxy resins derived from renewable resources, including resins of glycidyl ethers of plant-derived anhydrosugars and curing agents for curing the resin, wherein the curing agent is either plant-derived polyamines or polycarboxylic acids, or their derivates. The anhydrosugar is preferably a dianhydrosugar, more preferably a bisanhydrohexitol or isohexide, and most preferably isosorbide, isomannide, or isoidide.

In an embodiment of the invention, the epoxy includes a water-soluble resin of glycidyl ethers of plant-derived anhydrosugars and a water-soluble curing agent for curing the resin including either plant-derived polyamines or polycarboxylic acids, or their derivates, and the epoxy is cured by baking at an elevated temperature.

DETAILED DESCRIPTION OF PREFERRED EMBODIMENTS

The invention consists of novel epoxy thermoset resins derived from glycidyl ethers of anhydrosugars, especially isosorbide, isomannide, and isoidide, each of which may be derived from renewable resources, such as plant-derived glucose. The resins are cured by reaction with certain cross-linking agents, which themselves may also be bioderived agents, so that ideally the whole polymer composition is derived from renewable resources.

The synthesis of the glycidyl ethers of the bisanhydrohexitols may be performed by any known route, preferably using the reaction of the isohexide diols directly with epichlorhydrin. The most convenient route is that of Morrison (U.S. Pat. No. 3,041,300; loc. cit.) which uses excess epichlorohydrin as a reaction medium and aqueous alkali. The route of Zech and LeMaistre (U.S. Pat. No. 3,225,067), which uses additional organic solvents and reactive materials such as sodium hydride is less practicable. It is also possible to react isohexide diols with epichlorhydrin in a two-stage reaction sequence using cationic conditions. The first stage is to react the two components in the presence of Lewis acid catalysts, such as boron trifluoride etherate, stannous fluoride or Periodic Table Group IIIA metal salts to open the epoxide ring and form a chlorohydrin ether. This is dehydrochlorinated in a separate step by reaction with aqueous alkali to form the desired glycidyl ether (See, for example, U.S. Pat. No. 5,162,547 (Roth et al.) and U.S. Pat. No. 5,245,048 (Rolfe et al.)). Examples of the synthesis of isosorbide diglycidyl ether using aqueous alkali, using a non-aqueous solvent, and using the cationic (Lewis acid) routes are set out below.

The synthesis of the isohexide glycidyl ethers frequently does not give pure diglycidyl ethers in that oligomers may be formed by concomitant reaction of the epoxy function with unreacted isohexide diol. The product may be a mixture of oligomeric polyhydroxyethers linked by 2-hydroxypropylene-1,3-diether and 3-hydroxypropylene-1,2-diether links. The estimation of the epoxy content of the resin is measured by several methods well described in the literature: one method is to heat the weighed amount of resin with an aliquot of standardized pyridine hydrochloride in pyridine and back titrate the excess HCl with standardized methanolic potassium hydroxide. The amount of HCl consumed in the reaction is a direct measure of the number of epoxide groups present since each epoxide group reacts with one equivalent of HCl by ring opening to form a chlorohydrin ether. This method gives the epoxy equivalent in terms of epoxy groups per 100 gm resin. From this value the estimated molecular weight of the resin can be calculated.

Epoxy resins are hardened or cured by a cross linking reaction using one of three methods. The chemistry of epoxy curing is explained in great detail in *Handbook of Composites*, edited by S T Peters, Chapter 3, pp 48-74, published by Chapman & Hall, 1998, ISBN 0 412 54020 7. Application characteristics and final physical properties can be tailored by the choice of curing agent.

In the first method, the terminal epoxy functions react in the cold with polyamines of the general formula ($NH_2$—$R^1$—NH—$R^2$— . . . R"—$NH_2$) to give a cold curing resin composition. The ring opening of the epoxy ring with a primary or secondary amine generates an ethanolamine link, thus joining the oligomers by a stable C—N bond. Epoxy groups will potentially react with every —NH— unit, so that a simple diamine $NH_2$—R—$NH_2$ acts as a tetrafunctional crosslinker and reacts with four epoxy groups. Reaction of epoxy resins with polyamines such as triethylene tetramine or tetraethylene pentamine gives a highly crosslinked structure and such curing reactions may become very exothermic unless the reaction is carefully controlled. Similar curing reaction takes place with aromatic amines. In this case the reaction is usually carried out at elevated temperatures and the cured system will usually have a higher Tg than epoxies cured with aliphatic amines. Amide groups [—CONH—] will also react with epoxide rings but the rate of reaction is usually much slower than for amines.

In the second method the epoxy resin is reacted with a cyclic acid anhydride of the general formula:

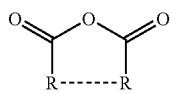

Structure I may react with both epoxy rings and any pendant hydroxyls. The reaction is more complex than at first sight and depends on initial ring opening of the anhydride to form a bipolar intermediate of the type [$OC^+$—R—R—$COO^-$]. For this reason a tertiary amine catalyst [$R_3N$] is usually added to initiate the reaction. The reactive dipolar species then attacks epoxy groups at both the anionic and the cationic sites and forms stable ester bonds which link the structure together. The reaction is self-perpetuating so that a high density of cross-links is produced. Acid anhydrides do not usually cold cure, but do react readily at elevated temperatures (80-150° C.).

The final method uses the epoxy resin itself, without any added curing agent, and depends on catalytic homopolymerization of the epoxy groups by a ring-opening polymerization mechanism initiated by a catalyst. Either Lewis acids or Lewis bases may be used to initiate this reaction.

For this invention, it is desirable that the curing agents also be derived from renewable resources and typical molecules that may be of use are amino acids and their derivatives (such as their lower alkyl esters) specifically those with polyfunctional groups. Examples would be cystine, lysine, ornithine, arginine and hydroxyproline. Various polyamino-peptides would also work. Other materials would include 2,5-dideoxy-2,5-bisamino-isosorbide (see structure II) and isosorbide 2,5-bis(3-aminopropyl)ether (structure III) and NN'-bis(3-aminopropyl) derivatives formed by cyanoethylation and hydrogenation of structure III. The corresponding derivatives of isomannide and isoiide would be included.

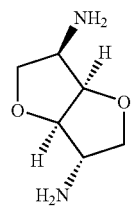

Structure II

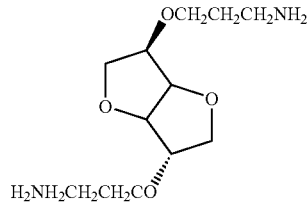

Structure III

Desirable curing agents would be the well-known commercial range of polyamino-amides derived from dimer acids by reaction with polyamines, which are marketed under the trade name VERSAMIDES®. These are derived from unsaturated fatty acids such as linoleic and linolenic acids widely available as glycerides in flax seed, sunflower seed, rapeseed etc. The acids are thermally dimerised to produce a mixture of alkylated cyclic polycarboxylic acids. Reaction of dimer acids with polyamines gives a polyfunctional polyamino-amide that is an excellent curing agent for epoxy resins.

There are many dicarboxylic acids that may be obtained from natural sources such as succinic acids and its anhydride, tartaric acid, malic acid, citric acid, mesaconic acid, citraconic acid, itaconic acid and their related anhydrides. Polyfunctional sugar acids which can form cyclic anhydrides and lactones may be useful curing agents, particularly if the reaction is catalyzed.

EXAMPLES

Example 1

Preparation of Isosorbide Diglycidyl Ether using Aqueous Alkali

Into a 1000 ml three-neck flask fitted with a Dean-Stark tube, condenser with exit bubbler tube, pressure-equalizing dropping funnel, gas inlet and sealed paddle stirrer were placed 29.2 g (0.20 moles) isosorbide, 200 ml dimethyl acetamide (DMAC) and 200 ml toluene. A slow stream of argon was passed through the apparatus to prevent oxidation. A solution of 16 g sodium hydroxide (0.40 moles) in 16 ml water was added drop-wise to the flask and the mixture stirred briskly and refluxed for 4 hours as water collected in the Dean-Stark tube. A total of 28 ml water was collected (the theoretical yield is 16 ml+7.2 ml=23.2 ml). Approximately 100 ml toluene was allowed to distil out from the system and 100 ml DMAC added. The hot mixture was left to cool somewhat and 1.0 ml 15-crown-5 ether added.

The Dean-Stark tube was replaced with a plain reflux condenser and 39 g (0.50 moles) epichlorohydrin added drop-wise to the warm reaction mixture with stirring, under an argon atmosphere. There was an exothermic reaction sufficient to cause the mixture to reflux gently without extraneous heat. When all the epichlorohydrin had been added, the mixture was refluxed and stirred for a total of 11 hours and left to cool overnight. A thick precipitate of sodium chloride settled out. The mixture was diluted with 1000 ml water and stirred without heating until the salt dissolved. A brown mixture was extracted with three portions of dichloromethane, the organic layer washed three times with 10% brine solution and finally dried over anhydrous sodium sulfate. Removal of the solvent on the rotary evaporator left a pale brown oil weighing 32.0 g (62% theoretical yield).

Example 2

Preparation of Isosorbide Diglycidyl Ether in a Non-Aqueous Solvent

Seven grams of isosorbide were dehydrated by refluxing under a Dean-Stark tube with toluene for two hours. The solvent was evaporated to dryness in a rotary evaporator. To 5.82 g (0.04 moles) freshly dried isosorbide was added 100 ml anhydrous dimethyl sulfoxide under anhydrous conditions and argon blanket and stirred and warmed to 50° C. It dissolved to give a clear pale brown solution. Sodium hydride dispersion in oil (equivalent to 0.08 moles) was weighed out quickly and added to the solution in which it dissolved rapidly with effervescence evolving hydrogen. After one hour no more gas was evolved and a precipitate separated out, presumably the insoluble sodium alkoxide. The mixture was stirred at 25° C. for 48 hrs, then 0.12 moles epichlorohydrin added and the mixture stirred under argon for another 48 hours at 25° C.

The mixture as added to 500 ml water and stirred for two hours, the final pH was 8.0. The product was extracted from the resulting aqueous mixture with 3 portions of chloroform. The combined chloroform extracts were washed three times with 10% brine, and dried over sodium sulfate. Removal of the solvent gave an oily emulsion containing some immiscible liquid, probably mineral oil from the sodium hydride. The mixture was dissolved in a little tetrahydrofuran, which left the oily impurity as a separate phase and it was separated off in a small tap funnel. Removal of the THF solvent left the product as an oil weighing 10.0 g (96% theoretical yield).

Example 3

Isosorbide Diglycidyl Ether Using a Cationic (Lewis Acid) Route

A three neck 500 ml flask fitted with a paddle stirrer, reflux condenser and a dropping funnel, was charged with 73 g (0.50 moles) solid isosorbide and heated in an oil bath under an argon atmosphere to 100° C. The solid melted to a colorless oil and the melt was stirred while stannous fluoride (1.6 g, 0.01 mole) catalyst was added and then 78 ml (1.0 moles) epichlorhydrin added drop-wise from the tap funnel. Initially the mixture went milky, but as the bath was raised to 130° C. and the epichlorhydrin began to reflux (bp 115-120° C.), the mixture went to a pale straw-colored homogeneous liquid. It was held at 130-135° C. for several hours and the color slowly went to a mid straw. The refluxing slowly ceased as the epichlorhydrin all reacted.

After cooling overnight, the mixture was diluted with 150 ml toluene and a solution of 40 g (1.0 mole) sodium hydroxide in 40 ml water was added drop-wise with brisk stirring from the tap funnel under an argon blanket. After three hours the mixture was added to 500 ml deionized water and the precipitated salt dissolved. The orange mixture was separated to remove the toluene layer and the aqueous layer extracted three times with toluene and once with ethyl acetate, the combined organic layers were washed with 100 ml portions of 10% potassium dihydrogen phosphate solution to remove alkali, dried over sodium sulfate and evaporated to give 25.2 g (20% theoretical yield) of a pale yellow oil.

Example 4

Large Scale Preparation of Epoxy Resin from Isosorbide and Epichlorhydrin using Aqueous Sodium Hydroxide A 5-liter 5-neck flask was fitted with a sealed paddle stirrer, an inverted pattern Dean and Stark water-separator tube (for solvents heavier than water), reflux condenser, long stem thermometer dipping well into the reaction flask, a 500 ml pressure-equalizing tap funnel fitted with a Kontes "Varibor"™ stopcock, and an inlet and outlet for inert gas (nitrogen or argon) to blanket the reaction. All ground glass joints were protected with PTFE sleeves to prevent the glassware from seizing up under the influence of strong aqueous alkali. The flask was charged with 584 gm (4.00 moles) "Cerestar" brand isosorbide, and 3700 gm (40.0 moles) of 98% epichlorhydrin. The mixture was sparged with nitrogen gas and stirred and brought to a gentle reflux under a slow stream (2 bubbles per second) of nitrogen gas. The reaction flask temperature was 115° C. and the still head 112° C. The stirrer was set to 260 rpm.

Meanwhile a solution of 320 gm (8.0 moles) sodium hydroxide was dissolved in 320 mls distilled water and, after cooling, the caustic alkali solution was added to the P.E. tap funnel. When the reaction was steadily refluxing, the Varibor™ stopcock was adjusted to allow a slow stream of alkali (about 2-3 drops/minute) to be added to the reaction flask. This was to avoid any sudden exothermic reaction. It was found very desirable that the alkaline solution be dropped directly into the liquid mixture and not allowed to run down the insides of the reaction flask, as this eventually would lead to a large aggregates of crystalline sodium chloride encrusted on the walls of the reactor. Gradually, water began to appear as an upper layer in the D-S tube and the reaction was left to proceed steadily.

Periodically, water was run off from the Dean-Stark tube which was fitted with a 3-way stopcock for this purpose. The reaction mixture was initially clear and pale yellow but soon went cloudy with precipitated salt and gradually became a thick slurry of liquid and precipitated solid. The rate of addition of base was speeded up somewhat after three hours and the whole addition step took about 12 hours.

By this time 458.5 mls water (98.5% theory, allowing for the added water) were collected. The reaction was run for another 45 minutes to ensure no more water was forming as a layer above the organic phase in the D-S tube. The reaction was left to cool and stand overnight under a slow nitrogen stream. Next day the mixture was filtered through large sintered glass funnel to remove the sodium chloride and the filtrate collected. The solid on the funnel was washed several times with acetone but the acetone washings were kept separate at this time from the first filtrate. Both filtrates were taken down separately on a rotary evaporator and the excess epichlorhydrin was recovered for redistillation and re-use from the first filtrate. The first batch yielded 917 gms of resin (88.9% theory) and the second (acetone) batch left 76 gms. The combined yield was 992 gm, 96% theory, as a viscous pale yellow resin. Approximately 900 gm of epichlorhydrin was recovered by redistillation.

The recovered and dried sodium chloride weighed 460 g, 98% theory. The epoxy equivalent of the resin, as measured by reaction with an aliquot of standard pyridine hydrochloride in excess pyridine under nitrogen at 100 C and subsequent back titration with standard methanolic potassium hydroxide using phenolphthalein as indicator was 223. This corresponds to an average resin molecular weight of 446 Daltons and indicates a dimeric structure with two isosorbide units joined with a 2-hydroxy-1,3-propane di-ether link and capped with glycidyl ether units.

Example 5

Curing with Nadic Methyl Anhydride

Nadic Methyl Anhydride (NMA) is common curing agent for epoxies. It is liquid at room temperature and can be readily mixed with epoxy resins. Cross linking is usually performed at elevated temperature with the aid of catalysts, because the reaction kinetics is relatively slow at low temperatures. Sixty grams (60 g) isosorbide epoxy (epoxy equivalent weight 230 g/eq) were mixed with 47 g NMA (anhydride equivalent weight of 180 g/eq) and with 0.6 g Benzyldimethylamine (BDMA), which is a well-known catalyst for such systems. Air bubbles were removed by pulling vacuum at room temperature for about 20 minutes and the mixture was poured into a preheated mold with a cavity of 0.125" thickness. Curing was performed for 3 hours at 110° C. and additional 16 hours at 150° C. The glass-cured epoxy was tested by Differential Scanning Calorimeter (DSC). The Glass Transition Temperature (Tg) was observed at 113° C. as a characteristic step change in the heat flow curve.

Example 6

Curing with Aliphatic Polyether Triamine

Aliphatic amines are commonly used curing agents for epoxy systems, which require room temperature, or moderated temperature curing conditions. Jeffamine T403 is a commonly used commercial liquid curing agent, which combines ease of handling, moderate curing kinetics and good mechanical properties. Sixty-one grams (61 g) isosorbide epoxy (epoxy equivalent weight 230 g/eq) were mixed at room temperature with 20.4 g Jeffamine T403 (hydrogen amine equivalent weight 76.9 g/eq). Air bubbles were removed from the mixture under vacuum for about 30 minutes. The mixture was poured into a 6×6×0.125" plaque cavity mold, which was preheated to about 100° C. Curing was performed in air oven for 4 hours at 100° C.

The molded plaque was cut by a high-speed router to tensile test specimens (ASTM D638 type V) and notched Izod specimens (ASTM D256). The tensile modulus and strength of the cured epoxy was 2900 MPa and 69 MPa respectively and the reversed notched impact energy (ASTM method E) was 12 ft-lb/in. The Glass Transition Temperature, measured by DSC method as the typical step change in the heat flow curve, was 48° C.

Example 7

Curing with Aliphatic Polyether Triamine in Water Solution

Isosorbide epoxy in the amount of 6.25 g (epoxy equivalent weight 230 g/eq) was dissolved in 10 g deionized water. Jeffamine T403 in the amount of 2.1 g (hydrogen amine equivalent weight 76.9 g/eq) was added to the solution. The amine dissolved completely and formed a clear solution. A small amount of the above solution was spread over a glass slide and left in open air to dry and cure at room temperature. The rest of the solution was sealed in a small vial. Within 24 hours the solution which was spread on the glass slide formed a clear solid coating of crosslinked epoxy, while the solution in the sealed vial formed a clear gel.

The same procedure was repeated with 5.0 g isosorbide epoxy and 1.8 g hardener T-403, which were dissolved in 54.5 g deionized water. The clear solution was placed in a sealed vial. Within 24 hours at room temperature the epoxy reacted with the hardener and formed a clear gel.

Example 8

Curing with 4,4'-Methylenedianiline

Methylenedianiline (MDA) is a solid material with a melting point of about 89° C. Full curing of such material with an epoxy resin requires mixing of the two materials, either in solution, or by melting the MDA in the epoxy. Twenty grams isosorbide epoxy (epoxy equivalent weight 230 g/eq) were heated to about 80° C. To this was added 4.31 g MDA (amine hydrogen equivalent weight 49.6 g/eq) and the system was stirred and heated until the MDA dissolved completely in the epoxy. The mixture was cured 2 hours at 80° C. and 16 hours at 120° C. in air and 2 more hours at 150° C. under vacuum. The cured epoxy was a solid material with clear amber color, typical of cured epoxy systems. The glass transition temperature (Tg) of the cured epoxy was measured after drying at 120° C., both by Differential Scanning Calorimeter (DSC) and by Thermo Mechanical Analysis (TMA) methods. In both tests the glass transition has a typical characteristic of an amorphous material and the measured Tg in both methods was about 89° C.

Example 9

Curing with
4,4'-(Hexafluoro-Isopropylidene)Diphthalic
Anhydride

Isosorbide epoxy in the amount of 1.6 g (epoxy equivalent weight 230 g/eq), and 1.54 g 4,4'-(hexafluoro-isopropylidene)diphthalic anhydride (anhydride equivalent weight of 222 g/eq) were mixed at room temperature with a mortar and pestle. The mixture was placed over night in a vacuum oven at 50° C. for degassing. The mixture, which had a consistency of a white viscous paste, was placed in a small mold with 0.5 mm deep cavity. The mold was heated in a press up to 250° C. and held at this temperature for 30 minutes before cooling. The solid epoxy film was removed from the mold and cut to 4 mm wide strips for testing.

Thermo Mechanical Analysis (TMA) was performed from room temperature to 250° C. The material remained solid throughout the test, indicating that the epoxy was crosslinked (cured). A $T_g$ of 200° C. was observed as a slope change in the expansion curve, which is the characteristic feature of the glass transition in polymers.

Example 10

Preparation of Isosorbide
2,5-bis-(2-Cyanoethyl)Ether

The method used was based upon that of Nishida, U.S. Pat. No. 6,541,587. In a 2000 ml 3-neck flask fitted with an Allihn condenser, a magnetic stir-bar and a long stem thermometer, were placed 146 gm (1.00 mole) dried isosorbide and 137 ml acrylonitrile. The flask was chilled in an ice bath to 10-15 C and a 2.0 ml of a 40% solution of benzyltrimethylammonium hydroxide (Triton-B) added. There was instantly a transient red coloration which quickly faded. The mixture was allowed to come to room temperature and stirred magnetically and further heated gently on a heating mantle while a further 100 ml acrylonitrile was added slowly. When the batch reached 47° C. the mixture began to warm up spontaneously, so the heat was removed and the exothermic reaction allowed to run its course. The mixture quickly warmed up until the acrylonitirile refluxed vigorously. To control the reaction, the flask was temporarily chilled in the ice bath again until it moderated. When the reaction had subsided, the mixture was allowed to stand for a time then heated to gentle reflux for 2-3 hours and left to cool.

A mixture of 2000 ml deionized water and 10 ml glacial acetic acid was added to neutralize the catalyst and the resulting cloudy pale orange liquid extracted thrice with 300 ml portions of dichloromethane to remove the product. The combined organic phase was washed twice with 10% brine solution and dried overnight over anhydrous sodium sulfate. After filtering, the solvent was removed on the Rotavapor and to leave a pale amber, rather viscous oil weighing 207.9 gm, (82.5% theory). The IR spectrum of the product as a liquid film showed a nitrile peak at 2240 cm$^{-1}$. NMR showed the sample to be at least 95% diether.

The ether had a high boiling point; microdistillation at 220° C./2 mB produced a small amount of distillate, but there was evidence of decomposition (reversion) in the still pot. The dinitrile was reduced on a small scale (500 mg) with hydrogen at 500 psi in methanol at 70° C. using a Raney cobalt catalyst. The equivalent amount of hydrogen was taken up. The resulting methanol solution of product was cooled, filtered to remove the catalyst and the methanol removed under reduced pressure. The $^1$H NMR spectrum of the product was consistent with at least 95% pure bis(3-aminopropyl)ether of isosorbide. This material was used directly to make the epoxy resin.

Example 11

Curing of Isosorbide Epoxy with Isosorbide Diamine

Isosorbide diamine (described in example 10) is liquid at room temperature and is soluble in water. Its formula weight is 260 g/eq. Isosorbide epoxy in the amount of 92.5 mg (epoxy equivalent weight 230 g/eq) was mixed with 25.5 mg isosorbide diamine (amine hydrogen equivalent weight 65 g/eq ). The two components mixed well. Four and one-half milligrams (4.5 mg) of the epoxy mixture were placed in a differential scanning calorimetry (DSC) pan, which was heated at a rate of 10° C./min from room temperature to 150° C. The DSC curing run shows an exothermic peak, centered around 90° C., which starts at about 30° C. and ends at about 150° C. The rest of the epoxy mixture was spread over a glass slide and cured for 16 hour in an oven at 80° C. The cured epoxy sample was scanned by DSC and it shows a step change at 39° C., which is characteristic of glass transition temperature. Both curing experiments demonstrate that the isosorbide epoxy can be cured with isosorbide diamine and that the reaction kinetics and cured properties of the epoxy mixture are within the range that can be expected from curing of epoxies with aliphatic amines.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

We claim:

1. An epoxy derived from renewable resources, comprising:
   (a) a resin comprising glycidyl ethers of plant-derived anhydrosugars; and
   (b) a curing agent selected from the group consisting of bis(3-aminopropyl)ethers of isosorbide, isomannide, and isoidide; and bisamines derived by replacement of the hydroxyl groups in isosorbide, isomannide, or isoidide with amino groups for curing the resin.

2. An epoxy, comprising:
   (a) a water-soluble resin comprising glycidyl ethers of plant-derived anhydrosugars;
   (b) a water-soluble curing agent for curing the resin selected from the group consisting of bis(3-aminopropyl)ethers of isosorbide, ismannide, and isoidide; and bisamines derived by replacement of the hydroxyl groups in isosorbide, isomannide, or isoidide with amino groups; and
   (c) wherein the epoxy is cured at room temperature.

* * * * *